(12) United States Patent
Trail et al.

(10) Patent No.: US 10,143,076 B2
(45) Date of Patent: Nov. 27, 2018

(54) SHIELDING STRUCTURES FOR LINEAR ACCELERATORS

(71) Applicant: Varian Medical Systems, Inc., Palo Alto, CA (US)

(72) Inventors: Mark E. Trail, Menlo Park, CA (US); Blake H. Gaderlund, Mountain View, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 211 days.

(21) Appl. No.: 15/097,007

(22) Filed: Apr. 12, 2016

(65) Prior Publication Data

US 2017/0295638 A1 Oct. 12, 2017

(51) Int. Cl.
*H05H 7/22* (2006.01)
*A61N 5/10* (2006.01)
*H05H 9/00* (2006.01)

(52) U.S. Cl.
CPC .............. *H05H 7/22* (2013.01); *A61N 5/1077* (2013.01); *H05H 9/00* (2013.01); *A61N 2005/1094* (2013.01); *A61N 2005/1095* (2013.01)

(58) Field of Classification Search
CPC .......... H05H 7/22; H05H 9/00; A61N 5/1077; A61N 2005/1094; A61N 2005/1095; H01J 27/02; H01J 27/028; H01J 37/08; H01J 1/00; H01J 1/54
See application file for complete search history.

(56) References Cited

U.S. PATENT DOCUMENTS

| | | | | |
|---|---|---|---|---|
| 9,642,239 | B2 * | 5/2017 | Kephart | H05H 7/22 |
| 9,721,748 | B2 * | 8/2017 | Seryi | H01J 35/02 |
| 9,789,341 | B2 * | 10/2017 | Abbasi | A61N 5/1077 |
| 2005/0078796 | A1 | 4/2005 | Leek | |
| 2017/0094770 | A1 * | 3/2017 | Kephart | H05H 7/22 |
| 2017/0265290 | A1 * | 9/2017 | Shvartsman | H05H 7/04 |
| 2017/0265291 | A1 * | 9/2017 | Nighan, Jr. | H05H 7/22 |
| 2017/0319872 | A1 * | 11/2017 | Galyaev | A61N 5/1049 |

FOREIGN PATENT DOCUMENTS

| | | |
|---|---|---|
| JP | H1050499 A | 2/1998 |
| JP | 2000200699 A | 7/2000 |
| JP | 2003036999 A | 2/2003 |
| JP | 2005085473 A | 3/2005 |
| WO | 2004093501 A2 | 10/2004 |
| WO | 2016194635 A1 | 12/2016 |

OTHER PUBLICATIONS

United Kingdom Intellectual Property Office, Search Report in United Kingdom Application No. GB1705371.1, Sep. 12, 2017, 2 pages.

\* cited by examiner

*Primary Examiner* — Joseph L Williams
*Assistant Examiner* — Jose M Diaz

(57) ABSTRACT

An apparatus includes an accelerator guide and a shielding structure enclosing the accelerator guide. The accelerator guide includes an electron source at a first end, a target at a second end, and a plurality of accelerating cavities coupled in series along a longitudinal axis between the first end and the second end. The accelerator guide has a contour as viewed in the longitudinal axis. The shielding structure has an inner wall surface defining a contour as viewed in the longitudinal axis generally conformal to the contour of the accelerator guide.

38 Claims, 6 Drawing Sheets

SHIELDING STRUCTURES FOR LINEAR ACCELERATORS

TECHNICAL FIELD

Embodiments of this disclosure relate generally to radiotherapy equipment. In particular, various embodiments of compact, integrated shielding structures for linear accelerators are described.

BACKGROUND

Radiation machines such as medical linear accelerators are useful in producing high energy radiation to treat patients with cancer. Depending on the type of cancer, position, size of the tumor and its surrounding critical organs, and the patient size, medical linear accelerators may operate at high energies ranging from about 4 MV to about 20 MV for radiation therapy procedures. To ensure safety, protective measures such as various radiation shielding must be taken to limit unwanted radiation to patients outside the planned treatment field and to radiotherapists and the general public to an acceptable level.

FIGS. 1A and 1B schematically show a conventional beehive or shielding structure 10 for a linear accelerator. The beehive 10 includes plural rows e.g. six rows as shown of lead stacked vertically to surround an accelerator guide. Each of the stacks is further cut into multiple pieces e.g. two to four pieces as shown to keep the weight manageable for someone to install or remove the accelerator guide. In the conventional beehive 10 shown in FIGS. 1A and 1B, each of the gaps and bolt clearance holes represents a potential radiation leakage path. Further, removing or installing an accelerator guide requires removal of all the heavy pieces of lead, which is labor intensive and can be dangerous as the guide must be removed while oriented in the vertical position high above the floor (about 8 to 9 feet high).

In conventional production implementation shown in FIG. 1C, the magnetic shield 12, a part serving to shield an accelerator guide 14 from variations in earth's magnetic field during rotation, is a separate piece part installed around the guide 14 prior to adding the lead shielding pieces described above. Mechanical alignment of the guide 14 with respect to the isocenter is done using a tripod feature 16. The tripod feature 16 extends radially outside the base 11 of the beehive 10 so that access to the jacking screws 18 and retention bolts 20 is possible. When alignment of the guide 14 is performed, the guide 14 is tilted and shifted laterally by adjusting the screws 18 and bolts 20 on the tripod feature 16 and lateral adjustment bolts 22 on the head frame 24. During the alignment, the lead beehive (10 in FIG. 1A) remains stationary while the guide 14 and tripod 16 translates or tilts. One limitation of the conventional design and implementation is that it requires mechanical clearance to avoid collisions of the guide 14 with the beehive 10 and magnetic shield 12 etc. The added clearance results in larger clearance holes for the tripod feature 16 which must be blocked with additional shielding extensions to the beehive 10. The increased clearance also causes increased shielding diameter to provide the required attenuation, which increases cost, weight, and volume taken up in the gantry.

SUMMARY

Certain embodiments of linear accelerators and compact, integrated shielding structures are set forth below. It should be understood that these embodiments are presented merely to provide the reader with a brief summary of certain forms the invention might take and that these embodiments are not intended to limit the scope of the invention. Indeed, the invention may encompass a variety of embodiments or aspects that may not be set forth below.

An apparatus comprises an accelerator guide and a shielding structure enclosing the accelerator guide. The accelerator guide comprises an electron source at a first end, a target at a second end, and a plurality of accelerating cavities coupled in series along a longitudinal axis between the first end and the second end. The accelerator guide has a contour as viewed in the longitudinal axis. The shielding structure has an inner wall surface defining a contour as viewed in the longitudinal axis. The contour of the inner wall surface of the shielding structure is generally conformal to the contour of the accelerator guide.

An apparatus comprises an accelerator guide and a shielding structure enclosing the accelerator guide. The accelerator guide comprises an electron source at a first end, a target at a second end, and a plurality of accelerating cavities coupled in series along a longitudinal axis between the first end and the second end. The shielding structure comprises a mono-block operable to hold the accelerator guide at least in a horizontal orientation. In some embodiments, the mono-block is configured to surround at least a major portion of the accelerator guide.

An apparatus comprises an accelerator guide and a shielding structure enclosing the accelerator guide. The accelerator guide comprises an electron source at a first end, a target at a second end, and a plurality of accelerating cavities coupled in series along a longitudinal axis between the first end and the second end. The accelerator guide comprises a guide-slide at the second end providing a contact surface engaging the inner wall surface of the shielding structure when the accelerator guide slides in or out of the shielding structure. In some embodiments, the guide-slide has a contour generally in an obround or oval shape to provide clearance to structures on the accelerator guide.

A shielding structure comprises a radiation shield and a magnetic shield. The radiation shield and magnetic shield are integrated in the form of a mono-block providing an internal volume configured to surround at least a major portion of an accelerator guide.

A method is provided for installing an accelerator guide in a shielding structure and/or removing an accelerator guide out of a shielding structure. According to the method, the accelerator guide and the shielding structure are oriented so that the accelerator guide remains in a substantially horizontal position when the accelerator guide is slidably placed in or removed out of the shielding structure.

Other embodiments are described in the Detail Description.

BRIEF DESCRIPTION OF THE DRAWINGS

These and various other features and advantages will become better understood upon reading the following detailed description in conjunction with the accompanying drawings and the appended claims provided below, where:

DETAILED DESCRIPTION

Figures 1A, 1B:
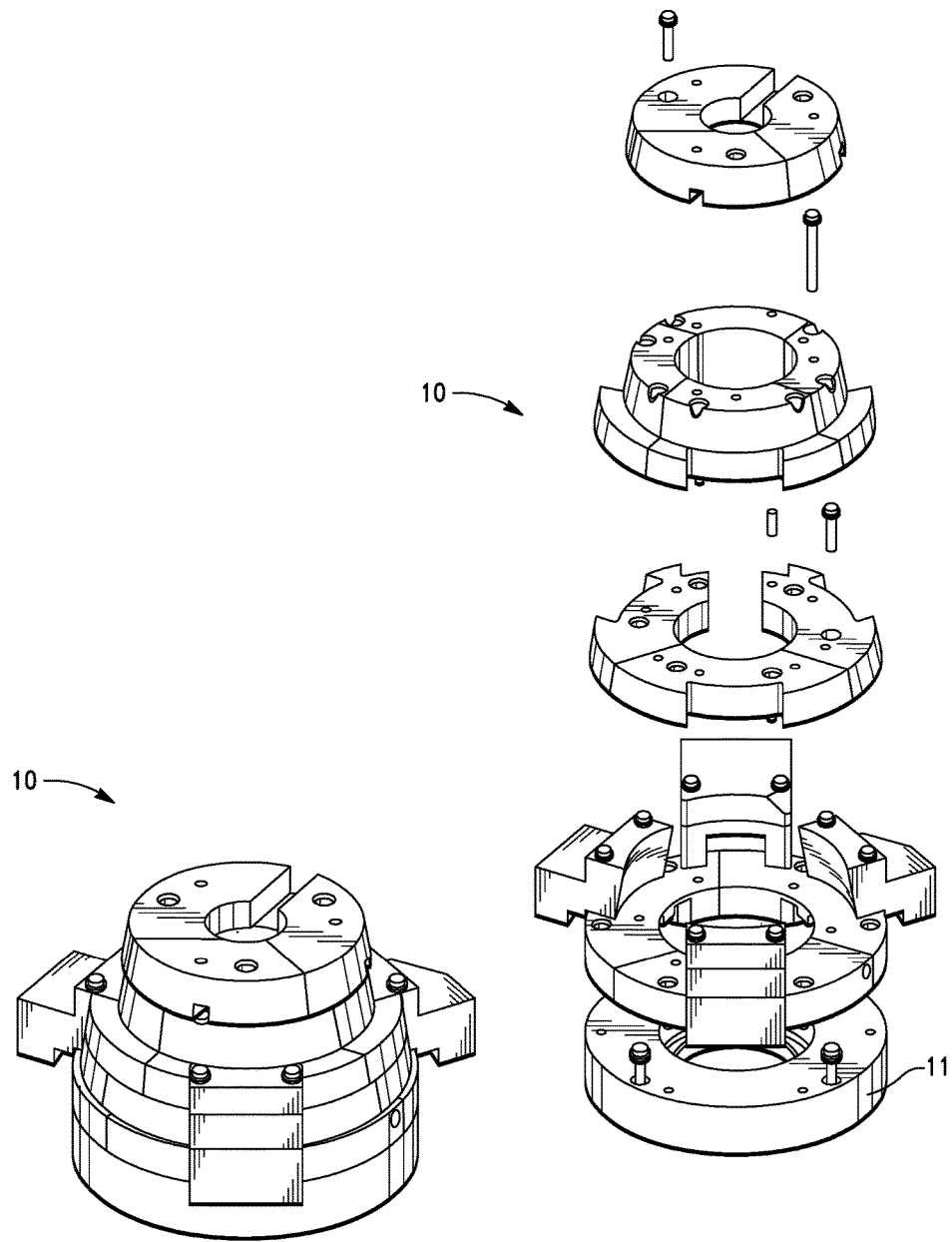
FIG. 1A schematically shows a conventional shielding structure for an accelerator guide.
FIG. 1B is an exploded view of the conventional shielding structure shown in FIG. 1A.
Figure 1C:
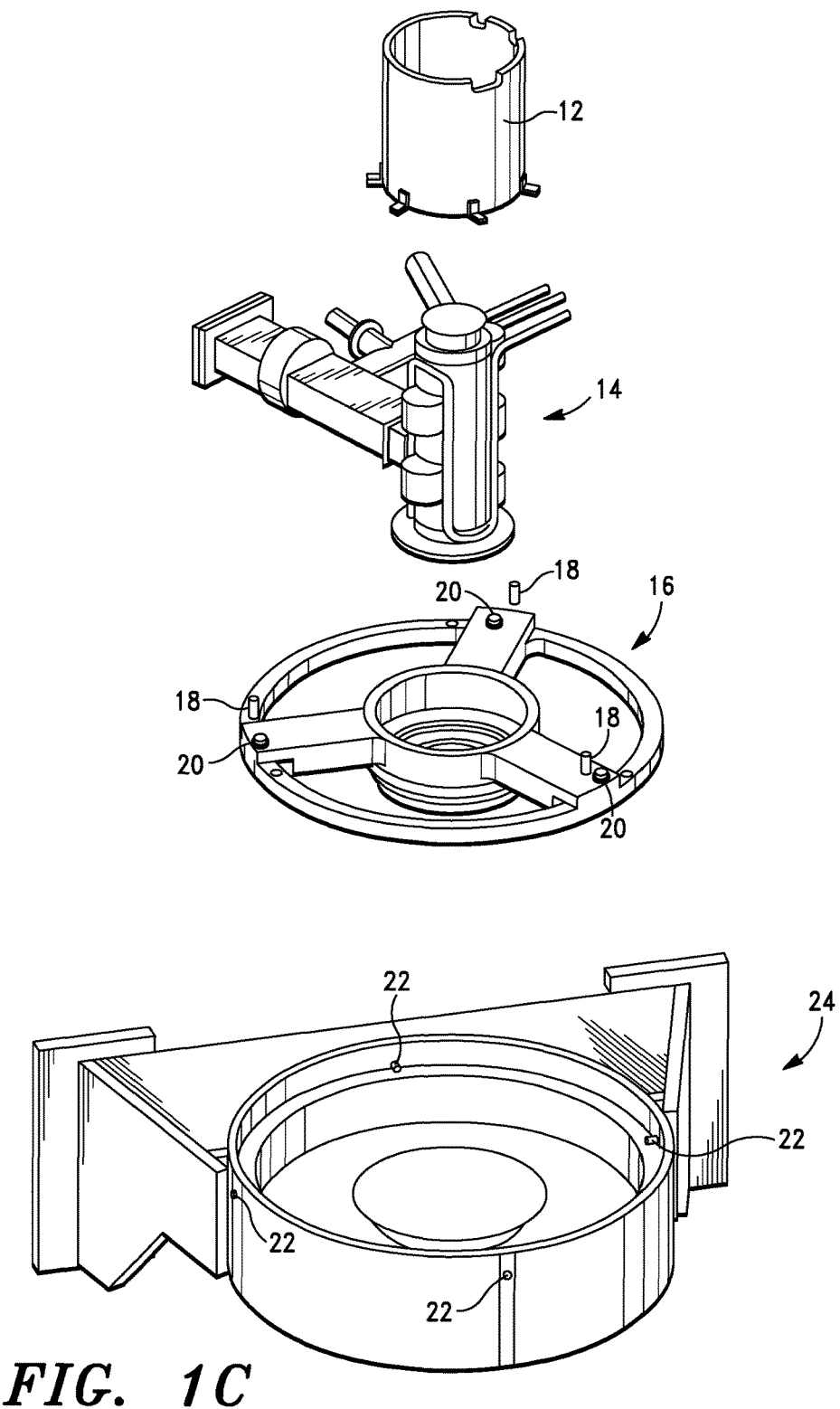
FIG. 1C is an exploded view showing a conventional installation method of an accelerator guide.

Various embodiments of linear accelerators and shielding structures are described. It is to be understood that the disclosure is not limited to the particular embodiments described as such. An aspect described in conjunction with a particular embodiment is not necessarily limited to that embodiment and can be practiced in any other embodiments.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise.

As used herein, the term "accelerator guide" or "guide" refers to a component of an electron linear accelerator, which includes an electron gun, a target, and plural accelerating cavities coupled in series between the electron gun and the target.

As used herein, the terms "beehive" and "shielding structure" may be used interchangeably and refer to a structure that encloses an accelerator guide to shield guide glow and scattered target radiation.

As used herein, the phrase "a major portion of an accelerator guide" refers to more than 50% of the volume of an accelerator guide body including the accelerating and side cavities but excluding the gun end and target end. As an example, if an accelerator guide body were cut in cross-section along a longitudinal axis, the accelerator guide would be approximately equally divided (50%-50%).

As used herein, the term "integral," "integrated," or other grammatical equivalents refers to an embodiment where two or more functional components are constructed such to be used as a unit.

As used herein, the term "mono-block" refers to a single piece of a shielding structure. A mono-block may include two or more functional components which are integrated or constructed in a single unit. As an example, a mono-block may include a radiation shield configured to attenuate radiation and a magnetic shield configured to redirect a magnetic field. The magnetic shield and radiation shield may be integrated to form a mono-block of a shielding structure to perform dual-shielding functions.

Embodiments of the disclosure will now be described with reference to FIGS. 2-8. It should be noted that some figures are not necessarily drawn to scale. The figures are only intended to facilitate the description of specific embodiments, and are not intended as an exhaustive description or as a limitation on the scope of the disclosure. Further, in the drawings, some specific details may be shown in order to provide a thorough understanding of the disclosure. It will be apparent however to one of ordinary skill in the art that some of these specific details may not be employed to practice embodiments of the disclosure. In other instances, well known components may not be shown in detail in order to avoid unnecessarily obscuring the embodiments of the disclosure.

Figure 2:
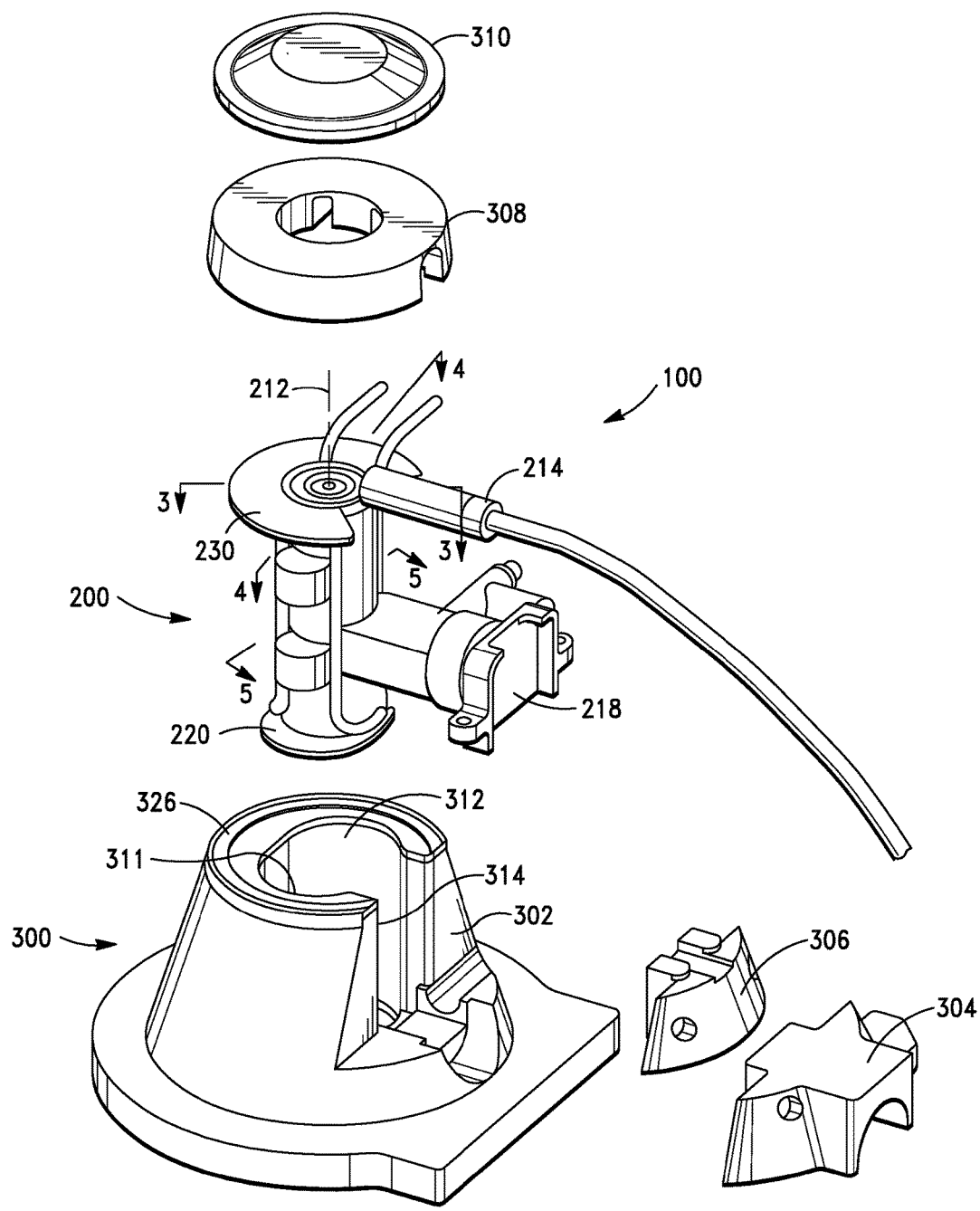
FIG. 2 is an exploded view of a radiation apparatus showing an accelerator guide and a shielding structure according to embodiments of the disclosure.

In an aspect, the disclosure provides a radiation apparatus 100 including an accelerator guide 200 and a shielding structure 300, as better viewed in FIG. 2. FIG. 2 is an exploded view of the radiation apparatus 100, showing the accelerator guide 200 before being installed in or after being removed out of the shielding structure 300. The accelerator guide 200 is constructed or configured to produce radiation such as x-rays suitable for radiotherapy as will be described in greater detail below. The shielding structure 300 may include plural shielding blocks 302-310 constructed or configured to enclose the accelerator guide 200 to shield for accelerator guide glow and scattered target radiation.

As will be embodied in greater detail below, the shielding structure 300 of the disclosure is designed, constructed or configured to conform or tightly conform to the contour of the accelerator guide 200. The tight conformity brings the shielding structure 300 close to the accelerator guide 200 or the source of radiation, which leads to reduction of the total weight and volume of shielding needed and minimizing the shielding cost. The tight conformity also allows the accelerator guide 200 and the shielding structure 300 to be moved as a unit, e.g. tilted and/or shifted together when the accelerator guide 200 is angle- and/or position-aligned with the isocenter.

Figure 3:
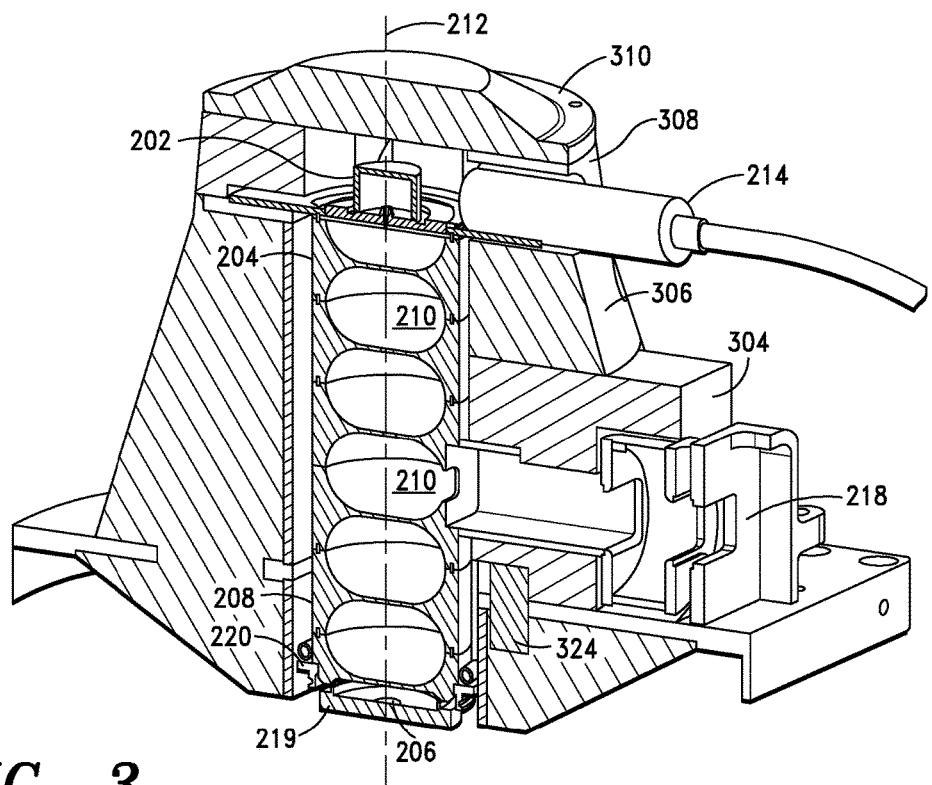
FIG. 3 is a cross-sectional view of the radiation apparatus shown in FIG. 2 taken along line 3-3 after the accelerator guide is installed in the shielding structure according to embodiments of the disclosure.
Figure 4:
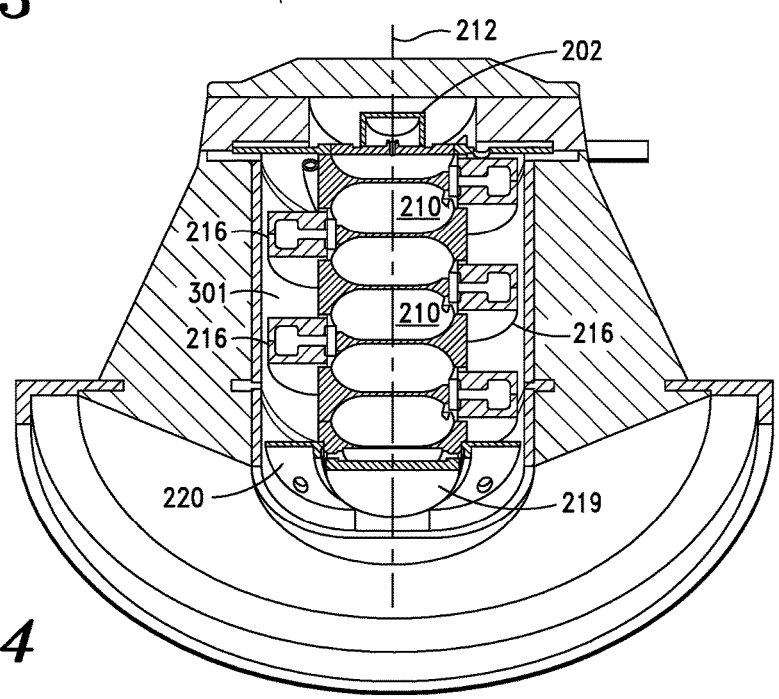
FIG. 4 is a cross-sectional view of the radiation apparatus shown in FIG. 2 taken along line 4-4 after the accelerator guide is installed in the shielding structure according to embodiments of the disclosure.

The accelerator guide 200 may include an electron source 202 at a first end 204, a target 206 at a second end 208, and plural accelerating cavities 210 coupled in series along a longitudinal axis 212, as better viewed in FIGS. 3 and 4. FIGS. 3 and 4 are cross-sectional views of the radiation apparatus 100 shown in FIG. 2 taken along lines 3-3 and 4-4 respectively after the accelerator guide 200 is installed in the shielding structure 300. As shown, the electron source 202 may be an electron gun connected to an electrical source (not shown) via a feedthrough 214 and configured to inject continuous or pulsed electrons into the accelerating cavities 210. The plural accelerating cavities 210 may be aligned to permit passage of electron beams through beam central apertures (not shown). The plural accelerating cavities 210 can be electromagnetically coupled via plural side cavities 216. As shown, each of the side cavities 216 may couple two adjacent accelerating cavities 210. A waveguide 218 may be coupled to one of the accelerating cavities 210 to deliver microwave power from a source (not shown) to the accelerator guide 200. The target 206 may be supported on a substrate 219 at the second end 208. The target 206 may comprise tungsten or other high density metals which generate x-rays upon impingement by electrons produced by the electron source 202 and accelerated by the accelerating cavities 210. In embodiments of the disclosure, the accelerator guide 200 may be designed and constructed to generate x-rays having an energy level ranging from about 1 to 20 MeV.

Returning to FIG. 2, the shielding structure 300 may include plural shielding blocks 302-310, which when assembled, form an enclosure to shield accelerator guide glow and scattered target radiation. The enclosure has an inner wall surface 311 defining an internal volume for receiving the accelerator guide 200. According to embodiments of the disclosure, the shielding structure 300 or the plural shielding blocks 302-310 may be designed or configured to form an internal volume that conforms to the contour of the accelerator guide 200. By way of example, the accelerator guide 200 may have a contour as viewed in the longitudinal axis 212. The inner wall surface 311 of the enclosure may define a contour as viewed in the longitudinal axis 212 generally conformal to the contour of the accelerator guide 200. As an example, the accelerator guide 200 may have a contour generally in an oval or abround shape as viewed in the longitudinal axis 212. The inner wall surface 311 of the enclosure may correspondingly have a contour generally in an oval or obround shape as viewed in the longitudinal axis 212 to conform to the contour of the accelerator guide 200.

Figure 5:
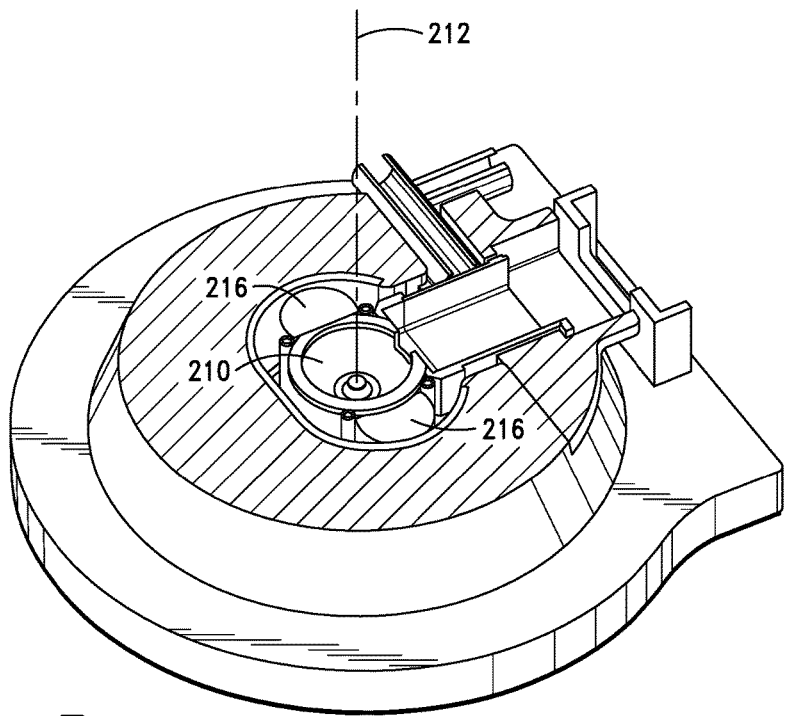
FIG. 5 is a cross-sectional view of the radiation apparatus shown in FIG. 2 taken along line 5-5 after the accelerator guide is installed in the shielding structure according to embodiments of the disclosure.
Figure 6:
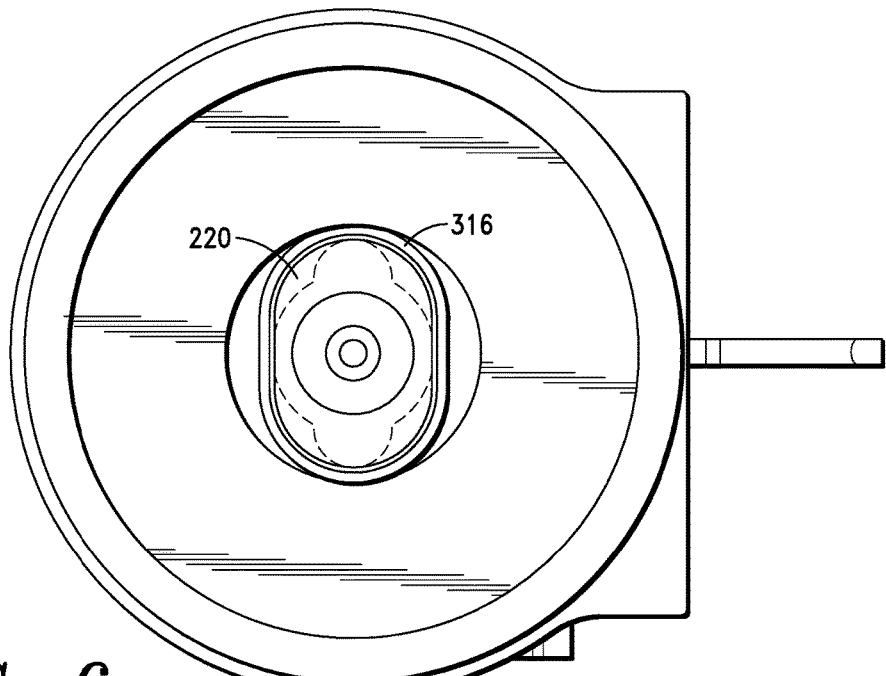
FIG. 6 is a bottom view of the radiation apparatus shown in FIG. 2 after the accelerator guide is installed in the shielding structure according to embodiments of the disclosure.

FIG. 5 better shows an exemplary contour of the accelerator guide 200 as viewed in the longitudinal axis 212. FIG. 5 is a cross-sectional view of the radiation apparatus 100 shown in FIG. 2 taken along line 5-5 after the accelerator guide 200 is installed in the shielding structure 300. As viewed in the longitudinal axis 212, the exemplary contour of the accelerator guide 200 may be partially defined by an accelerating cavity 210 generally in a circular shape and partially defined by two side cavities 216 generally in a semi-circular shape. The circular accelerating cavity 210 may define a first dimension, and the combined semi-circular side cavities 216 and circular accelerating cavity 210 may define a second dimension. It is possible that the shielding structure 300 or the shielding blocks 302-310 are designed or constructed to form an internal volume having a contour as viewed in the longitudinal axis 212 that generally conforms to the contour defined by both the side cavities 216 and the accelerating cavity 210. Alternatively, as will be described in greater detail below, the accelerator guide 200 may include a guide-slide 220 located at the second end 208 (FIGS. 2-4). The guide-slide 220 may be generally oval-shaped or obround-shaped as viewed in the longitudinal axis 212 and sized to accommodate both the first dimension of the accelerating cavity 210 and the second dimension of the combined side cavities 216 and accelerating cavity 210. In such embodiment, the contour of the accelerator guide 200 as viewed in the longitudinal axis 212 may be defined by the guide-slide 220 and the shielding structure 300 or the shielding blocks 302-310 may be designed or constructed to form an internal volume that generally conforms to the contour defined by the guide-slide 220, as shown in FIG. 6 and will be described in greater detail below.

It should be noted that the accelerator guide 200 may be constructed to have a contour in other shapes and the shielding structure 300 or the shielding blocks 302-310 may be designed or constructed to form an internal volume having a contour in other shapes to conform to the contour of the accelerator guide 200 in various other shapes. The principle of the disclosure is not limited to a particular contour shape of the accelerator guide 200 and the internal volume defined by the shielding structure 300.

Referring to FIG. 4, when the accelerator guide 200 is installed in the shielding structure 300, space 301 may exist between adjacent side cavities 216 or between the accelerating cavities 210 and the shielding structure 300. Additional shielding pieces (not shown) may be disposed in the space 301 to further improve shielding. In alternative embodiments, lead or tungsten BBs, tungsten loaded epoxy, or other suitable radiation attenuating materials may fill any gaps and/or joints that may exist to further improve shielding.

Returning to FIG. 2, in some embodiments of the disclosure, the shielding structure 300 may include a mono-block 302 which surrounds a major portion of the accelerator guide 200 when being installed. As shown, the exemplary mono-block 302 may include an opening 312 that allows for the accelerator guide 200 to be placed in or removed out of the shielding structure 300, and a cut-away 314 providing clearance for the waveguide 218 coupled to the accelerator guide 200 when the accelerator guide 200 is slidably placed in or removed out of the shielding structure 300. In the exemplary embodiment shown in FIG. 2, the mono-block 302 can surround the entire accelerator guide 200 except for the portion adjacent to the waveguide 218 which would be exposed in the cut-away 314, and the gun end portion which would be exposed in the opening 312. The exposed portion near the waveguide 218 may be covered by smaller shielding pieces 304 and 306. The exposed gun end portion near the opening 312 may be covered by a smaller shielding piece 308 and an end cap 310. FIG. 3 shows the smaller shielding pieces 304-306 covering the guide portion near the waveguide 218 and the shielding piece 308 and end cap 310 covering the gun end portion when the accelerator guide 200 is installed in the shielding structure 300.

The use of a mono-block surrounding a major portion of an accelerator guide leads to significant reduction of the total number of pieces of shielding blocks in the shielding structure 300 and associated mounting hardware, and thus minimizes gaps or joints in the shielding structure to reduce possible radiation leaks. According to embodiments of the disclosure, the total number of shielding pieces in a conventional beehive and associated mounting hardware can be reduced significantly by approximately 75%.

It should be noted that the exemplary mono-block 302 depicted in FIG. 2 is provided for illustration purpose and the disclosure is not limited to this particular example. While about half or more portion of an accelerator guide may be surrounded by a mono-block and the remaining portion of the accelerator guide and gun end are covered by smaller shielding pieces as shown in FIGS. 2-3, the principle of the disclosure can also be applied in situations where a mono-block surrounds less than half portion of an accelerator guide but nonetheless can stably hold the entire accelerator guide in a horizontal orientation, which allows the accelerator guide to be slidably placed in or removed out of the shielding structure, as will be described in greater detail below.

Figure 8:
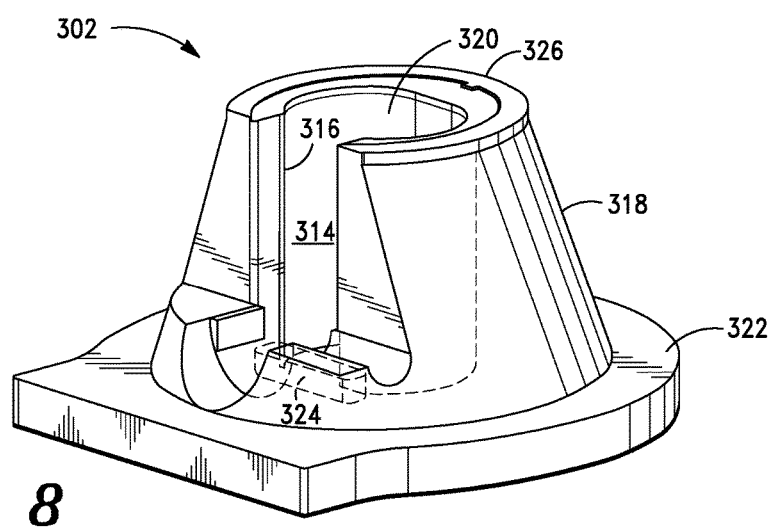
FIG. 8 is a perspective view of a shielding structure showing a magnetic shield integrated with a radiation shield according to embodiments of the disclosure.

FIG. 8 schematically shows an exemplary mono-block 302 of a shielding structure according to embodiments of the disclosure. As shown, the mono-block 302 includes a magnetic shield 316 and a radiation shield 318. The magnetic shield 316 and radiation shield 318 are integrated in the form of a mono-block, providing an internal volume 320 configured to surround at least a major portion of an accelerator guide.

The magnetic shield 316 serves to shield an accelerator guide from variations in earth's magnetic field during rotation, which could inadvertently steer the beam generated by the guide. The magnetic shield 316 may be made of iron, steel or any other suitable ferromagnetic metals or alloys which can redirect magnetic field. The magnetic shield 316 may also serve as a part of a mold for pouring or creation of the radiation shield 318. The magnetic shield 316 may be generally in a tubular shape with a cut-away in the side to provide clearance for a waveguide as described above. The magnetic shield 316 may define a volume for receiving or holding a portion or a major portion of an accelerator guide. The magnetic shield 316 may have a cross-sectional contour generally conformal to the contour of an accelerator guide. For example, the magnetic shield 316 may define an oval, obround or other suitable shape as viewed in a longitudinal axis to tightly conform to the contour of an accelerator guide.

The radiation shield 318 can be made of lead or other high density, radiation attenuating materials. The radiation shield 318 can be constructed by casting using the magnetic shield 316 as a part of the mold over a supporting plate 322. Structural elements (not shown in FIG. 8) may be used to support or stabilize the magnetic shield 316 on the plate 322 when the radiation shield 318 is cast and formed. As shown in FIG. 8, the thickness of the radiation shield 318 varies with the spatial location with respect to the target. This is mainly due to the spatial distribution of radiation generated by the target. When electrons strike a target, x-ray photons generated propagate largely in a forward direction to an isocenter or patient for treatment. There is a considerable angular spread in the resulting x-ray photons. Some photons backscatter, i.e., propagate at 180 degrees with respect to the electron beam direction. The distribution of x-ray photons generated is a function of spatial angles, and may be effected by the energy of the electrons striking the target, the geometric configuration of the target, the material composition of the target, etc. As a result, the thickness of the radiation shield 318 may also vary depending on its spatial angle in order to limit radiation leakage outside the shield below a generally uniform threshold value as required by e.g. International Electrotechnical Commission (IEC). Additional higher density shielding such as a tungsten block 324 as shown may be disposed or cast-in-place in a predetermined location to help compensate for the lack of shielding which is taken out for receiving a waveguide or its components in the radiation shield 318.

Still referring to FIG. 8, the mono-block 302 may include a mounting interface 326 providing features for mounting an accelerator guide to the mono-block 302 as will be described in greater detail below. Interface features 328 may be provided near the cut-away 314 for securing smaller shielding pieces (FIG. 2) after the accelerator guide is placed in the mono-block. Features such as steps, recesses or the like may be provided near the cur-away 314 to accommodate a waveguide and associated components.

Figure 7:
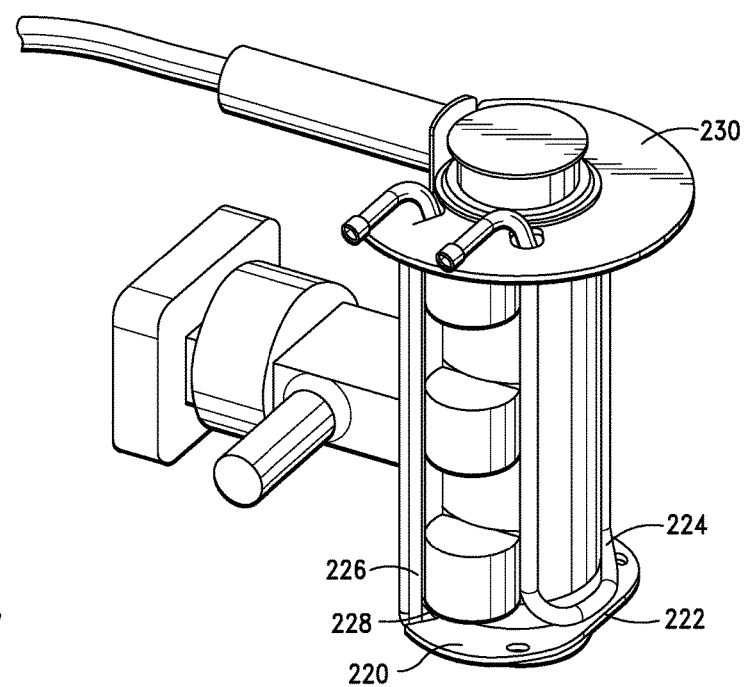
FIG. 7 is a perspective view of an accelerator guide showing some details of a guide-slide, side cavities, and waterlines according to embodiments of the disclosure.

Returning to FIG. 2 and also referring to FIGS. 6 and 7, in some embodiments of the disclosure, the accelerator guide 200 may include a guide-slide 220. The guide-slide 220 facilitates installation and/or removal of the accelerator guide 200 by providing a contact surface 222 with the shielding structure 300. The contact surface 222 of the guide-slide 220 allows the accelerator guide 200 to slide into or out of the shielding structure 300 while protecting the accelerator guide 200 e.g. side cavities 216 and waterlines 224-226 from collisions and damages.

The guide-slide 220 may be located at the second end 208 (target end) of the accelerator guide 200. For example, the guide-slide 220 may be coupled to the substrate 219 which supports the target 206. The guide-slide 220 has a contour as viewed in the longitudinal axis 212. The contour of the guide-slide 220 may be substantially conformal to the contour of an accelerating cavity 210 and side cavities 216 combined as viewed in the longitudinal axis 212. In alternative embodiments, the contour of the guide-slide 220 may be slightly different but accommodate the first dimension of the accelerating cavity and the second dimension of the combined side cavities and accelerating cavity as described above.

FIG. 6 is a bottom view of the radiation apparatus 100 shown in FIG. 2 after the accelerator guide 200 is installed in the shielding structure 300. By way of example, the guide-slide 220 as depicted in FIG. 6 may have an obround shape as viewed in the longitudinal axis, which has a first dimension slightly larger than the dimension defined by an accelerating cavity, and a second dimension slightly larger than the dimension defined by both an accelerating cavity and two side cavities coupled to the accelerating cavity. Waterlines 224-226, which circulate coolants for dissipating heat generated during acceleration of electrons and production of x-rays, can be disposed within the first and/or second dimensions of the guide-slide 220, as better viewed in FIG. 7, to protect them from collisions or damages during installation and/or removal of the accelerator guide 200. Alternatively, slots 228 may be provided in the peripheral of the guide-slide 220 to accommodate the waterlines 226 as better viewed in FIG. 7.

The use of the guide-slide 220 allows for tight conformity of the shielding structure 300 to the accelerator guide 200 while at same time protects the side cavities of the guide and waterlines from collisions and damages when the accelerator guide 200 slides in and out of the shielding structure 300. The use of guide-slide 220 also allows the mounting and/or removing of an accelerator guide in the horizontal position. As described above, conventional shielding structures include plural rows of lead stacked vertically to surround an accelerator guide, and each of the stacks is further cut into multiple pieces to keep the weight manageable for someone to install or remove the accelerator guide. Removing or installing an accelerator guide requires removal of all the heavy pieces of lead while the guide is oriented in the vertical position. This is both labor-intensive and dangerous because the installing and/or removing have to be carried out high above the floor.

According to embodiments of the disclosure, in mounting an accelerator guide the accelerator guide and the shielding structure may be oriented such that the longitudinal axis of the accelerator guide is substantially horizontal. The accelerator guide may be then slid into the shielding structure while the guide remains substantially horizontal. Likewise, in removing the accelerator guide out of the shielding structure, the accelerator guide and the shielding structure may be oriented such that the longitudinal axis of the guide is substantially horizontal. The accelerator guide can be then removed e.g. by sliding from the shielding structure while in the horizontal orientation.

Mounting and removing an accelerator guide in the horizontal position eliminates the risks of danger that would incur in the conventional method performed high above the floor. Further, mounting and removing an accelerator guide in the horizontal position avoids the need for increasing the height of ceiling, which would otherwise be required if the accelerator guide has to be removed out of the shielding structure in a vertical position in which case more ceiling clearance would be needed.

Returning to FIG. 2, in some embodiments of the disclosure, the accelerator guide 200 may be secured to the shielding structure 300 by a mounting flange 230. The mounting flange 230 may be coupled to first end 204 (gun end) of the accelerator guide 200, e.g. integrated with the anode plate of the electron gun. As described above in connection with FIG. 8, in some embodiments the shielding structure 300 may include a mono-block 302 having a mounting interface 326. As such, the mounting flange 230 may secure the accelerating guide 200 to the mono-block 302 by connecting the mounting flange 230 to the mounting interface 326 of the mono-block 302. Features such as openings or slots may be provided in the mounting flange 230 for the waterlines 324-326 and feedthrough 214. The accelerator guide 200, when secured to the shielding structure 300, may be moved together with the shielding 300 structure during angle- and/or position-alignment with respect to the isocenter.

Various embodiments of radiation apparatuses and shield structures for accelerator guides have been described. Those skilled in the art will appreciate that various other modifications may be made within the spirit and scope of the invention. All these or other variations and modifications are contemplated by the inventors and within the scope of the invention.

What is claimed is:

1. An apparatus, comprising:
an accelerator guide comprising an electron source at a first end, a target at a second end, and a plurality of accelerating cavities coupled in series along a longitudinal axis between the first end and the second end, the accelerator guide having a contour as viewed in the longitudinal axis;
a shielding structure enclosing at least the electron source and the plurality of accelerating cavities of the accelerator guide, the shielding structure having an inner wall surface defining a contour as viewed in the longitudinal axis generally conformal to the contour of the accelerator guide.

2. The apparatus of claim 1, wherein the accelerator guide further comprises a guide-slide coupled at the second end, the guide-slide defining the contour of the accelerator guide as viewed in the longitudinal axis and providing a contact surface slidably engaging the inner wall surface of the shielding structure.

3. The apparatus of claim 2, wherein the guide-slide has a contour generally in an obround shape as view in the longitudinal axis.

4. The apparatus of claim 2, wherein the shielding structure comprises a mono-block surrounding at least a major portion of the accelerator guide.

5. The apparatus of claim 4, wherein the mono-block comprises a radiation shield and a magnetic shield integrated with the radiation shield.

6. The apparatus of claim 4, further comprising a mounting flange coupled to the first end of the accelerator guide for mounting the accelerator guide to the mono-block.

7. The apparatus of claim 6, wherein the accelerator guide and the shielding structure are movable as a unit during alignment of the accelerator guide.

8. The apparatus of claim 1, wherein the accelerator guide further comprises a plurality of side cavities each coupling two adjacent accelerating cavities, and wherein the contour of the accelerator guide comprises a first section defined by a portion of an accelerating cavity and a second section defined by two side cavities coupled to the accelerating cavity.

9. An apparatus, comprising:
an accelerator guide comprising an electron source at a first end, a target at a second end, and a plurality of accelerating cavities coupled in series along a longitudinal axis between the first end and the second end; and
a shielding structure enclosing the accelerator guide, wherein the shielding structure comprises a mono-block operable to hold the accelerator guide at least in a horizontal orientation,
wherein the mono-block comprises a cut-away providing clearance for a waveguide coupled to the accelerator guide.

10. The apparatus of claim 9, wherein the mono-block is configured to surround less than a major portion of the accelerator guide.

11. An apparatus comprising:
an accelerator guide comprising an electron source at a first end, a target at a second end, and a plurality of accelerating cavities coupled in series along a longitudinal axis between the first end and the second end; and
a shielding structure enclosing the accelerator guide, wherein the shielding structure comprises a mono-block operable to hold the accelerator guide at least in a horizontal orientation,
wherein the mono-block is configured to surround at least a major portion of the accelerator guide.

12. The apparatus of claim 11, wherein the mono-block comprises a radiation shield and a magnetic shield integrated with the radiation shield.

13. The apparatus of claim 11, wherein the accelerator guide has a contour as viewed in the longitudinal axis and the mono-block has an inner wall surface defining a contour as viewed in the longitudinal axis generally conformal to the contour of the accelerator guide.

14. The apparatus of claim 13, wherein the contour defined by the inner wall surface of the mono-block is generally in an obround shape.

15. The apparatus of claim 13, wherein the accelerator guide further comprises a guide-slide at the second end, the guide-slide providing a contact surface slidably engaging the inner wall surface of the mono-block.

16. The apparatus of claim 15, wherein the guide-slide has a contour generally in an obround shape as view in the longitudinal axis.

17. The apparatus of claim 13, wherein the mono-block comprises a mounting interface for mounting the accelerating guide to the mono-block.

18. The apparatus of claim 17, further comprising a mounting flange coupled to the first end of the accelerator guide for securing the accelerator guide to the mono-block via the mounting interface.

19. An apparatus, comprising:
an accelerator guide comprising an electron source at a first end, a target at a second end, and a plurality of accelerating cavities coupled in series along a longitudinal axis between the first end and the second end; and
a shielding structure enclosing at least the electron source and the plurality of accelerating cavities of the accelerator guide, the shielding structure having an inner wall surface surrounding the accelerator guide;
wherein the accelerator guide further comprises a guide-slide at the second end providing a contact surface slidably engaging the inner wall surface of the shielding structure.

20. The apparatus of claim 19, wherein the guide-slide has a contour as viewed in the longitudinal axis, and wherein the inner wall surface of the shielding structure has a contour as viewed in the longitudinal axis generally conformal to the contour of the guide-slide.

21. The apparatus of claim 20, wherein the contour of the guide-slide and the contour of the inner wall surface of the shielding structure are generally in an oval shape.

22. The apparatus of claim 20, wherein the contour of the guide-slide and the contour of the inner wall surface of the shielding structure are generally in an obround shape.

23. The apparatus of claim 20, wherein the shielding structure comprises a mono-block surrounding at least a major portion of the accelerator guide.

24. The apparatus of claim 23, wherein the mono-block comprises a radiation shield and a magnetic shield integrated with the radiation shield.

25. The apparatus of claim 24, wherein the mono-block comprises a mounting interface.

26. The apparatus of claim 25, further comprising a mounting flange coupled to the first end of the accelerator guide for securing the accelerator guide to the mono-block via the mounting interface.

27. The apparatus of claim 20, wherein the mono-block comprises a cut-away providing clearance for a waveguide coupled to the accelerator guide.

28. The apparatus of claim 19, wherein the accelerator guide comprises a plurality of side cavities each coupling two adjacent accelerating cavities, wherein adjacent side cavities of the accelerator guide form gaps therebetween.

29. The apparatus of claim 28, further comprising radiation attenuating materials disposed in the gaps, wherein the radiation attenuating materials comprise lead or tungsten BBs, tungsten loaded epoxy, or shielding pieces.

30. A shielding structure, comprising:
a radiation shield; and
a magnetic shield comprising a ferromagnetic metal or alloy, wherein the radiation shield and magnetic shield are integrated in the form of a mono-block providing an internal volume configured to surround at least a major portion of an accelerator guide.

31. The radiation shield structure of claim 30, wherein the mono-block comprises a cut-away in a side providing clearance for a waveguide coupled to the accelerator guide.

32. The radiation shield structure of claim 30, wherein the mono-block has a cross-sectional contour generally in an obround shape.

33. The radiation shield structure of claim 30, wherein the mono-block has a cross-sectional contour generally in an oval shape.

34. The radiation shield structure of claim 30, wherein the mono-block comprises a mounting interface allowing the accelerator guide to be secured to the mono-block at an end adjacent to an electron source of the accelerator guide.

35. A method of installing an accelerator guide in a shielding structure and/or removing an accelerator guide out of a shielding structure, the accelerator guide comprising an electron source at a first end, a target at a second end, and a plurality of accelerating cavities coupled in series along a longitudinal axis between the first end and the second end, wherein the shielding structure encloses at least the electron source and the plurality of accelerating cavities of the accelerator guide, comprising:
orienting the accelerator guide such that the longitudinal axis of the accelerator guide is substantially horizontal; and
removing the accelerator guide out of the shielding structure while the longitudinal axis of the accelerator guide remains substantially horizontal.

36. The method of claim 35, wherein the accelerator guide is slidably removed out of the shielding structure.

37. The method of claim 35, further comprising placing the accelerator guide in the shielding structure while the longitudinal axis of the accelerator guide remains substantially horizontal.

38. The method of claim 37, further comprising aligning the accelerator guide with an isocenter, wherein the accelerator guide and the shielding structure are moved as a unit during the aligning of the accelerator guide with the isocenter.

* * * * *